(12) United States Patent
Miyazaki

(10) Patent No.: US 9,052,266 B2
(45) Date of Patent: Jun. 9, 2015

(54) X-RAY CT APPARATUS

(71) Applicants: Kabushiki Kaisha Toshiba, Tokyo (JP); Toshiba Medical Systems Corporation, Otawara-shi (JP)

(72) Inventor: Hiroaki Miyazaki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 224 days.

(21) Appl. No.: 13/736,194

(22) Filed: Jan. 8, 2013

(65) Prior Publication Data

US 2013/0182818 A1    Jul. 18, 2013

(30) Foreign Application Priority Data

Jan. 13, 2012  (JP) ................................ 2012-004741

(51) Int. Cl.
| | |
|---|---|
| *A61B 6/04* | (2006.01) |
| *G01N 23/04* | (2006.01) |
| *A61B 6/00* | (2006.01) |
| *A61B 6/03* | (2006.01) |

(52) U.S. Cl.
CPC .............. *G01N 23/046* (2013.01); *A61B 6/032* (2013.01); *A61B 6/4241* (2013.01); *G01N 2223/419* (2013.01); *G01N 2223/612* (2013.01); *A61B 6/583* (2013.01)

(58) Field of Classification Search
USPC ............ 378/1, 4, 5, 16, 17, 21; 382/128, 131, 382/132
See application file for complete search history.

(56) References Cited

U.S. PATENT DOCUMENTS

| 8,000,434 B2 | 8/2011 | Ziegler et al. | |
|---|---|---|---|
| 2005/0220265 A1* | 10/2005 | Besson | 378/16 |
| 2007/0269000 A1* | 11/2007 | Partain et al. | 378/37 |
| 2011/0064293 A1 | 3/2011 | Takayama et al. | |
| 2013/0307923 A1* | 11/2013 | Inglese et al. | 348/36 |

FOREIGN PATENT DOCUMENTS

| CN | 101578535 A | 11/2009 |
|---|---|---|
| JP | 2011-80979 | 4/2011 |

OTHER PUBLICATIONS

Combined Office Action and Search Report issued Jul. 10, 2014 in Chinese Patent Application No. 201310003215.4 (with English translation of category of cited documents).

* cited by examiner

*Primary Examiner* — Nicole Ippolito
(74) *Attorney, Agent, or Firm* — Oblon, McClelland, Maier & Neustadt, L.L.P.

(57) ABSTRACT

An X-ray CT apparatus includes: a detector that detects X-rays that have passed through a subject; a data acquiring unit that, for each of predetermined energy bands, counts photons having an energy level included in the predetermined energy band, from among photons derived from the X-rays detected by the detector; an acquisition controlling unit that controls the data acquiring unit in such a manner that energy bands including energy levels which the photons representing substances that are not of interest have are each larger than an energy band including an energy level which the photons representing a substance of interest have, in accordance with an image taking condition under which an image taking process is performed on the subject; and an image reconstructing unit that reconstructs an X-ray CT image by using a counting result obtained by the data acquiring unit controlled by the acquisition controlling unit.

18 Claims, 8 Drawing Sheets

FIG.4
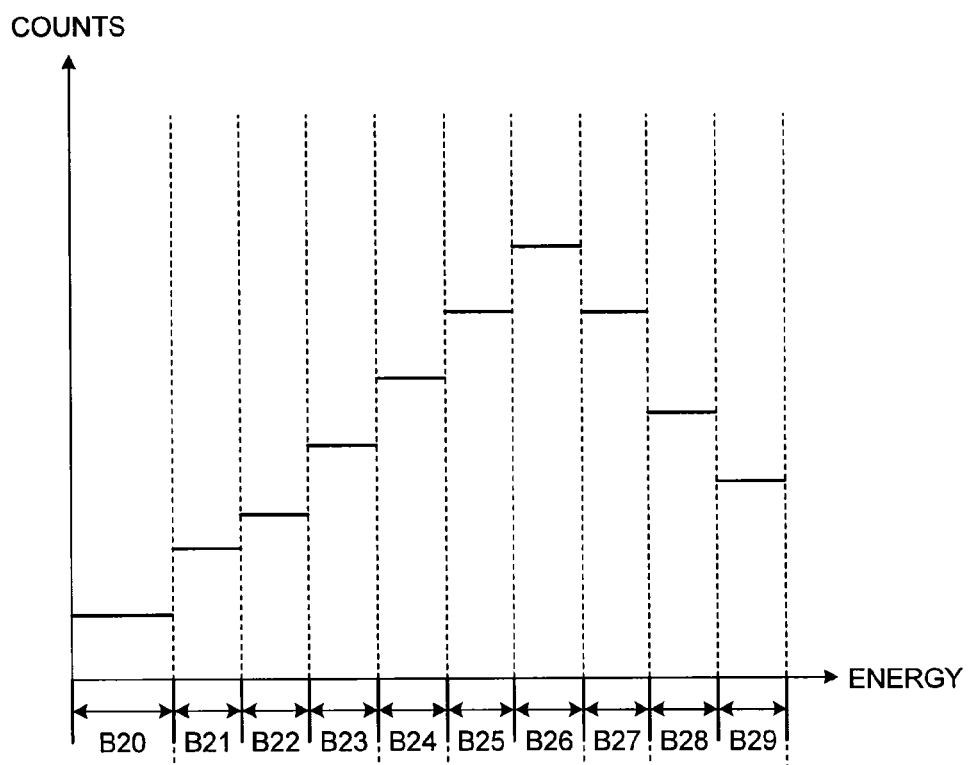
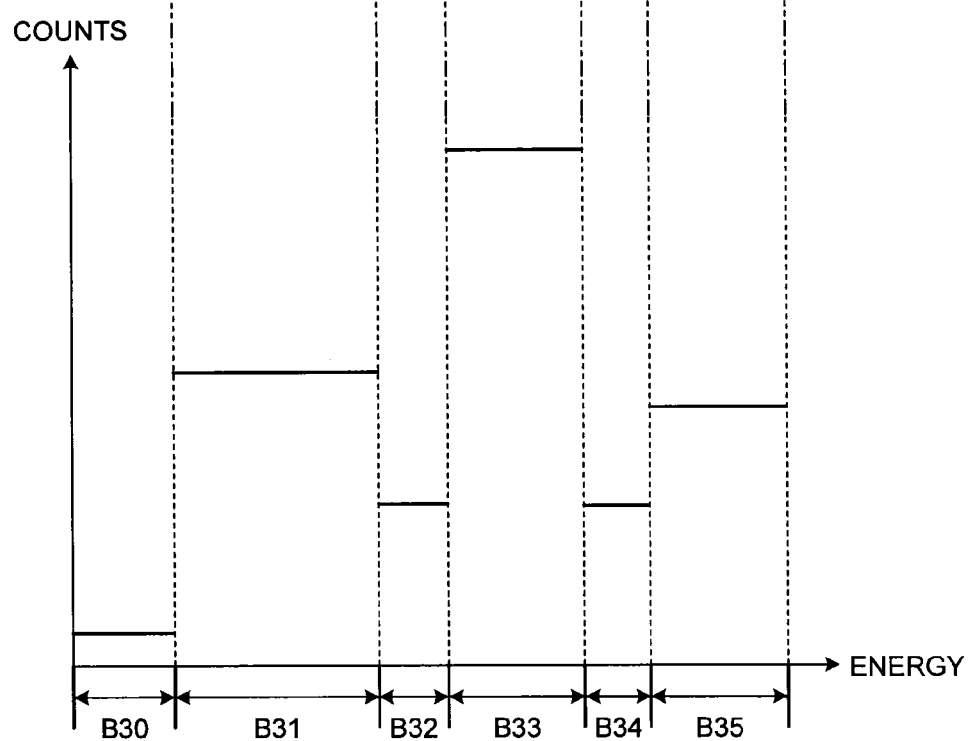

FIG.7
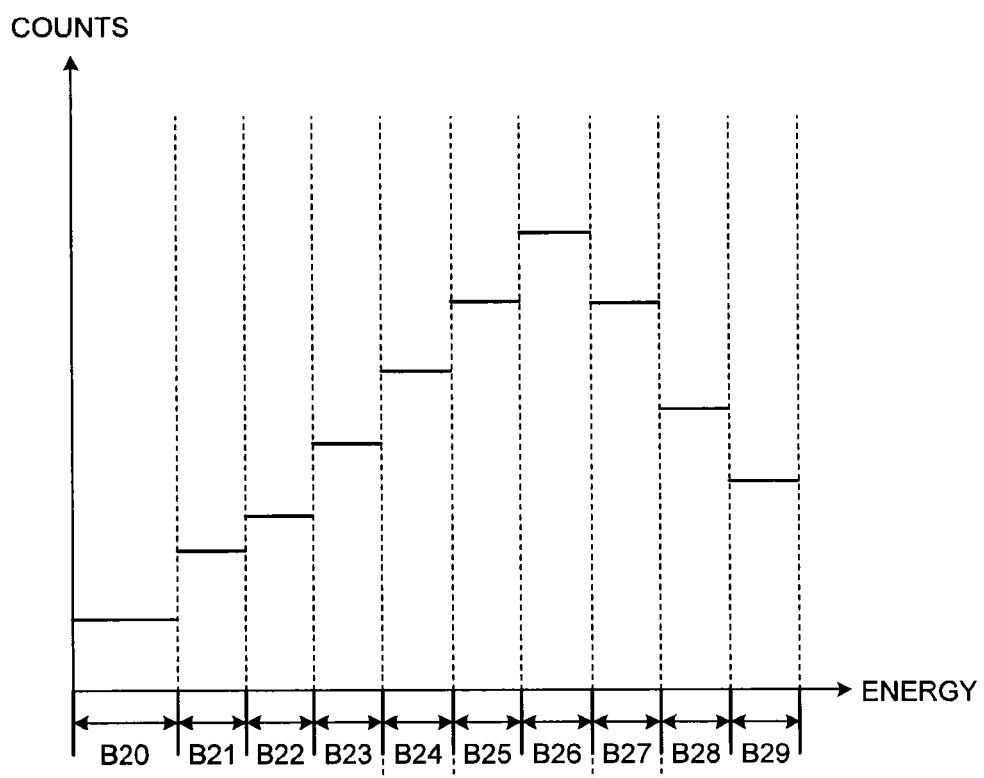
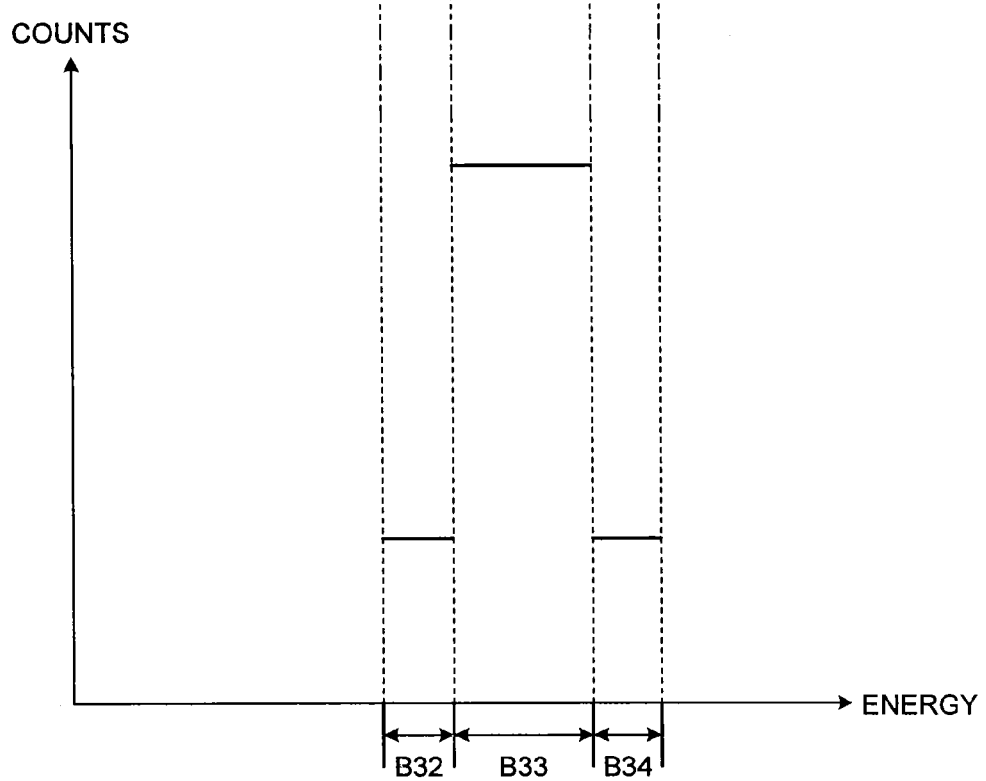

X-RAY CT APPARATUS

CROSS-REFERENCE TO RELATED APPLICATIONS

This application is based upon and claims the benefit of priority from Japanese Patent Application No. 2012-004741, filed on Jan. 13, 2012; the entire contents of which are incorporated herein by reference.

FIELD

Embodiments described herein relate generally to an X-ray Computed Tomography (CT) apparatus.

BACKGROUND

In recent years, X-ray Computed Tomography (CT) apparatuses that employ a photon-counting-method detector have been developed. Unlike integral-type detectors employed in conventional X-ray CT apparatuses, photon-counting-method detectors are configured to count photons derived from X-rays that have passed through an examined subject (e.g., "patient") for each of predetermined energy bands. Such X-ray CT apparatuses are configured to reconstruct an X-ray CT image based on a photon counting result.

BRIEF DESCRIPTION OF THE DRAWINGS

FIG. 4 contains charts of other examples of photon counting results;

FIG. 7 contains charts of yet other examples of photon counting results; and

DETAILED DESCRIPTION

An X-ray CT apparatus according to an embodiment includes a detector, a data acquiring unit, an acquisition controlling unit, and an image reconstructing unit. The detector detects X-rays that have passed through a subject. The data acquiring unit counts, for each of predetermined energy bands, photons having an energy level included in the predetermined energy band, from among photons derived from the X-rays detected by the detector. The acquisition controlling unit controls the data acquiring unit in such a manner that energy bands including energy levels of photons corresponding to substances that are not of interest have a larger width than a width of an energy band including an energy level of photons corresponding to a substance of interest, in accordance with an image taking condition under which an image taking process is performed on the subject. The image reconstructing unit reconstructs an X-ray CT image by using a counting result obtained by the data acquiring unit controlled by the acquisition controlling unit.

First Embodiment

An X-ray CT apparatus 1 according to a first embodiment is configured to radiate X-rays onto a subject from an X-ray tube and to reconstruct an X-ray CT image that indicates tissue morphological information on the inside of the subject P, by detecting X-rays that have passed through the subject P by employing a detector. It should be noted that the X-ray CT apparatus 1 according to the first embodiment is configured to reconstruct the X-ray CT image by counting the photons derived from the X-rays that have passed through the subject, by employing a photon-counting-method detector, and not an integral-type detector (which uses a current mode measuring method).

Figure 1:
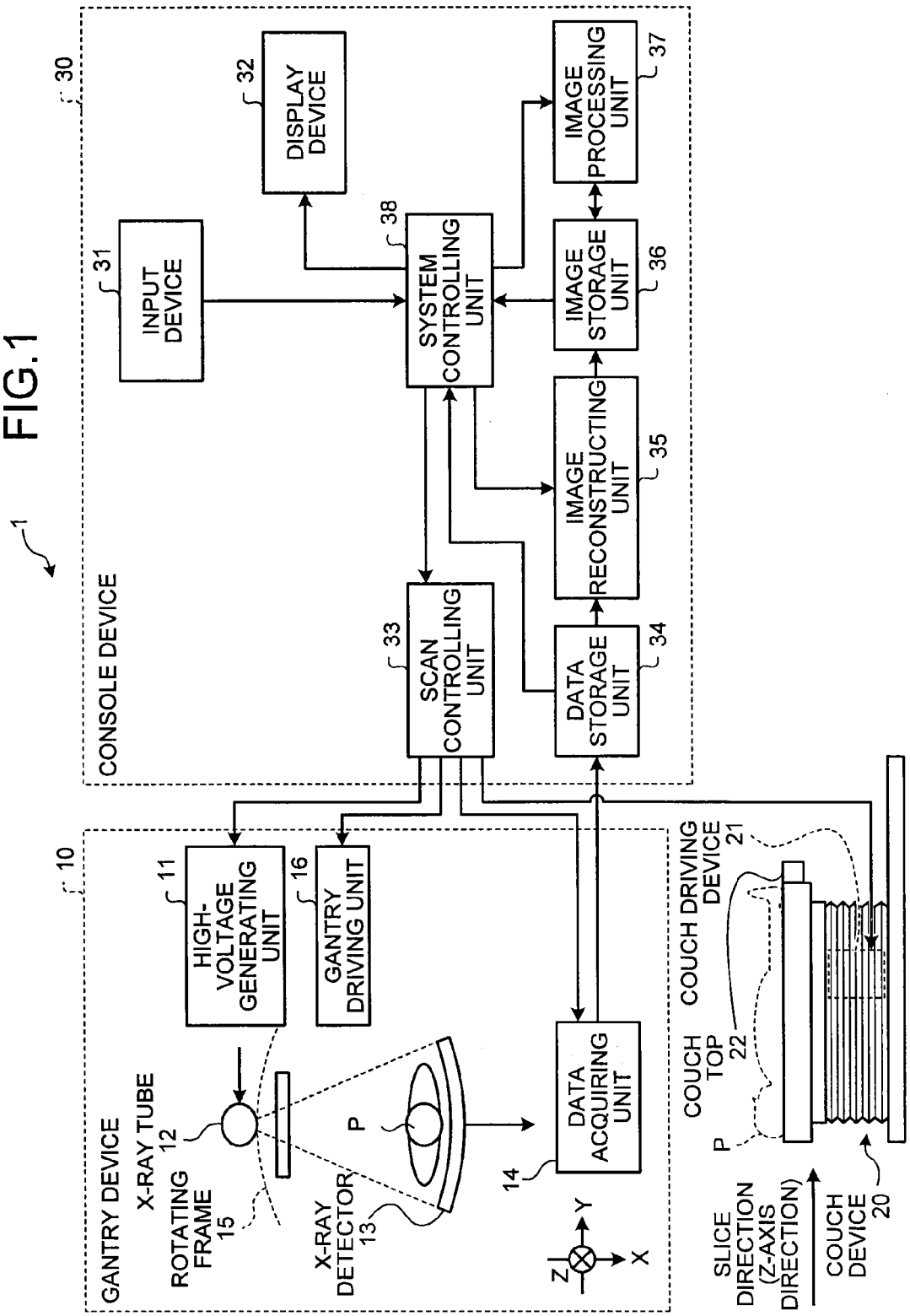
FIG. 1 is a block diagram of an exemplary configuration of an X-ray CT apparatus according to a first embodiment.

FIG. 1 is a block diagram of an exemplary configuration of the X-ray CT apparatus 1 according to the first embodiment. A high-voltage generating unit 11 is a device that supplies a high voltage to an X-ray tube 12. The X-ray tube 12 is a vacuum tube configured to radiate X-ray beams onto the subject P by using the high voltage supplied by the high-voltage generating unit 11. In conjunction with rotations of a rotating frame 15 (explained later), the X-ray tube 12 radiates the X-ray beams onto the subject P. In other words, the high-voltage generating unit 11 adjusts the dose of the X-rays radiated onto the subject P, by adjusting a tube voltage and a tube current supplied to the X-ray tube 12.

An X-ray detector 13 includes a plurality of detecting elements and detects, with the detecting elements, the X-rays that are generated from the X-ray tube 12 and have passed through the subject P. The detecting elements are configured with, for example, a scintillator array, a photodiode (PD) array, a circuit substrate, and the like. The scintillator array includes a plurality of scintillator blocks that are arranged in a channel direction and a slice direction and is configured to receive X-rays and generate fluorescence. The PD array includes a plurality of photodiodes and is configured to convert the fluorescence generated by the scintillator array into electric signals. The circuit substrate receives the electric signals resulting from the conversion by the PD array and outputs the electric signals to a data acquiring unit 14.

Under control of a scan controlling unit 33 (explained later), the data acquiring unit 14 counts photons derived from the X-rays detected by the X-ray detector 13. More specifically, the data acquiring unit 14 includes, for example, amplifiers, Analog to Digital Converters (ADCs), and the like. A set made up of an amplifier and an ADC operates as a charge reading circuit and is provided for each of the detecting elements included in the X-ray detector 13. The amplifiers are configured to amplify and to shape the waveforms of the X-ray signals detected by the X-ray detector 13. The ADCs are configured to apply an AD conversion to the signals amplified by the amplifiers and to count, for each of predetermined energy bands, the photons having an energy level included in the range of the energy band, by using comparators or the like. In other words, the data acquiring unit 14 operates as a pulse height discriminator circuit.

Further, for each of different phases (tube phases) of the X-ray tube 12, the data acquiring unit 14 acquires, as count information, a detection time at which the photons were detected, detection positions (the positions of the detecting elements included in the X-ray detector 13), and the photon counts corresponding to the energy bands and transmits the acquired count information to a data storage unit 34 (explained later). The photon counting process performed by the data acquiring unit 14 will be explained later.

In the following sections, an example will be explained in which the data acquiring unit 14 counts the photons by using the circuits including the amplifiers and the ADCs. However, it is also acceptable to configure the data acquiring unit 14 so as to include a counter that uses cadmium telluride (CdTe). In other words, it is acceptable to configure the data acquiring unit 14 so as to include a direct-conversion semiconductor detector that counts the photons derived from the X-rays, by directly converting the X-rays detected by the X-ray detector 13 into the photons.

The rotating frame 15 is an annular frame that supports the X-ray tube 12 and the X-ray detector 13 so as to oppose each other while the subject P is interposed therebetween and that is rotated by a gantry driving unit 16 (explained later) at a high speed on a circular trajectory centered on the subject P. By driving the rotating frame 15 to rotate, the gantry driving unit 16 causes the X-ray tube 12 and the X-ray detector 13 to turn on the circular trajectory centered on the subject P.

A couch device 20 is a device on which the subject P is placed. A couch driving device 21 moves a couchtop 22 in a Z-axis direction so as to move the subject P into the rotating frame 15. The couchtop 22 is a plate on which the subject P is placed.

A console device 30 is a device configured to receive an operation performed on the X-ray CT apparatus 1 by an operator and to generate a scanogram and/or to reconstruct the X-ray CT image from projection data acquired by a gantry device 10, by using the count information.

An input device 31 includes a mouse and/or a keyboard used by the operator of the X-ray CT apparatus 1 to input various types of instructions and various types of settings. The input device 31 is configured to transfer the instructions and information about the settings received from the operator to a system controlling unit 38. For example, the input device 31 receives an operation for setting an image taking mode from the operator. Examples of image taking modes include performing an image taking process on the subject P into whom a contrast agent has been administered (hereinafter, "contrast agent image taking process") and performing an image taking process while a site (e.g., a bone, a lung, the heart, or the like) inside the subject P is specified (hereinafter, "site specified image taking process").

A display device 32 is a monitor viewed by the operator. Under control of the system controlling unit 38, the display device 32 displays an X-ray CT image for the operator and displays a Graphical User Interface (GUI) used for receiving the various types of instructions and the various types of settings from the operator via the input device 31.

By following instructions from the system controlling unit 38, the scan controlling unit 33 controls the process to acquire the count information performed by the gantry device 10, by controlling the operations of the high-voltage generating unit 11, the data acquiring unit 14, the gantry driving unit 16, and the couch driving device 21.

The data storage unit 34 is configured with, for example, a semiconductor memory element such as a Random Access Memory (RAM) or a flash memory, a hard disk, an optical disk, or the like. The data storage unit 34 stores therein the photon counts for each of the energy bands, which is the count information acquired by the data acquiring unit 14. The data acquiring unit 14 and the data storage unit 34 are connected to each other by a data transfer path that allows contactless communication therebetween. For example, the data acquiring unit 14 and the data storage unit 34 are connected to each other by the contactless data transfer path configured with an optical communication unit that uses an LED or a laser, or a communication unit that implements a charge coupling method.

An image reconstructing unit 35 is configured to generate the projection data used for reconstructing the X-ray CT image, by performing a correcting process such as a logarithmic transformation process, an offset correction, a sensitivity correction, a beam hardening correction, and/or the like, on the count information stored in the data storage unit 34. Further, the image reconstructing unit 35 is configured to reconstruct the X-ray CT image by performing a back-projection process (e.g., a back-projection process using a Filtered Back Projection (FBP) method) on the generated projection data and to store the reconstructed X-ray CT image into an image storage unit 36.

Although not illustrated in the drawings, it is also acceptable to configure the X-ray CT apparatus 1 to include a pre-processing unit provided between the data acquiring unit 14 and the data storage unit 34. The pre-processing may be configured to generate the projection data by performing the correcting process such as a logarithmic transformation process, an offset correction, a sensitivity correction, a beam hardening correction, and/or the like, on the count information received from the data acquiring unit 14 via a contactless data transfer path and to store the generated projection data into the data storage unit 34. In that situation, the image reconstructing unit 35 reconstructs the X-ray CT image by performing a back-projection process on the projection data stored in the data storage unit 34.

The image storage unit 36 is configured with, for example, a semiconductor memory element such as a RAM or a flash memory, a hard disk, an optical disk, or the like and is configured to store therein the X-ray CT image reconstructed by the image reconstructing unit 35. An image processing unit 37 is configured to perform a post-processing process such as an artifact correcting process and/or other image processing processes based on instructions from the operator, on the X-ray CT image stored in the image storage unit 36 and to store the X-ray CT image on which the post-processing process has been performed into the image storage unit 36.

The system controlling unit 38 exercises overall control of the X-ray CT apparatus 1, by controlling the operations of the gantry device 10, the couch device 20, and the console device 30. More specifically, the system controlling unit 38 receives the count information from the gantry device 10 by controlling the scan controlling unit 33. Also, the system controlling unit 38 controls image processing processes performed by the console device 30, by controlling the image reconstructing unit 35 and the image processing unit 37. Further, the system controlling unit 38 exercises control so that the X-ray CT image stored in the image storage unit 36 is displayed on the display device 32. The system controlling unit 38 is configured with, for example, an integrated circuit such as an Application Specific Integrated Circuit (ASIC) or a Field Programmable Gate Array (FPGA) or an electronic circuit such as a Central Processing Unit (CPU) or a Micro Processing Unit (MPU).

As explained above, the X-ray CT apparatus 1 according to the first embodiment configured as described above reconstructs the X-ray CT image by counting the photons derived from the X-rays that have passed through the subject P, by employing the photon-counting-method X-ray detector 13 and the data acquiring unit 14. Further, under the control of the system controlling unit 38, the X-ray CT apparatus 1 according to the first embodiment reduces the amount of data transmitted from the data acquiring unit 14 to the data storage unit 34 and makes it possible to reconstruct an X-ray CT image desired by the operator.

Figure 2:
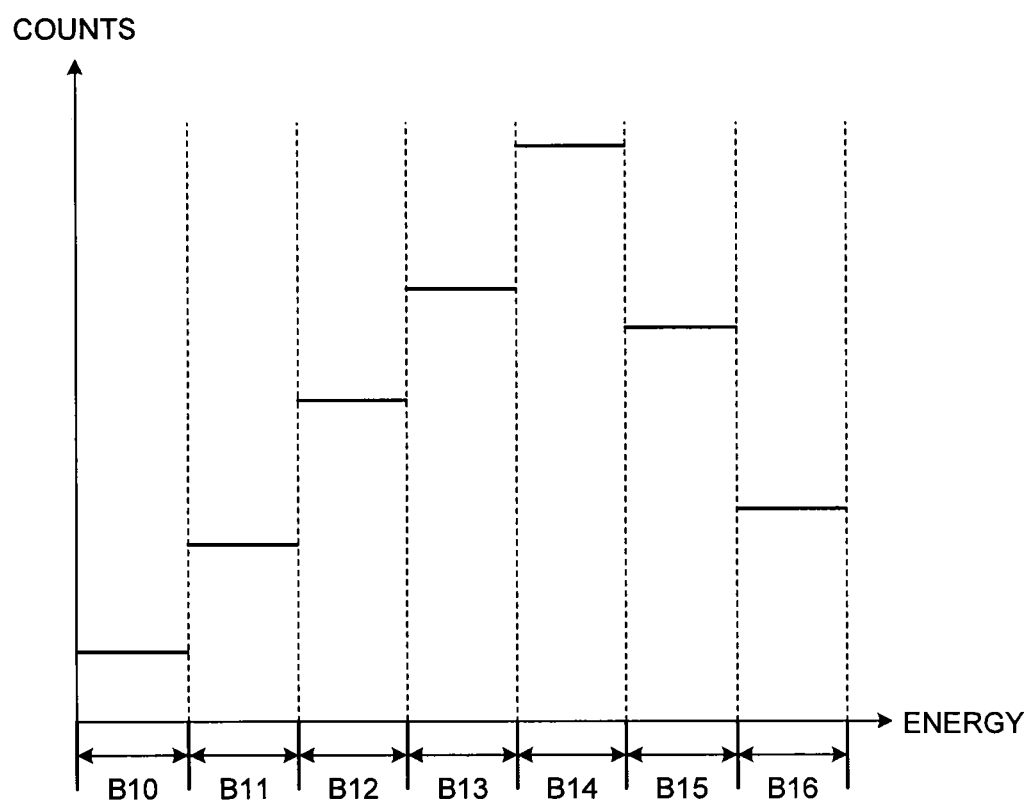
FIG. 2 is a chart of an example of a photon counting result.
Figure 3:
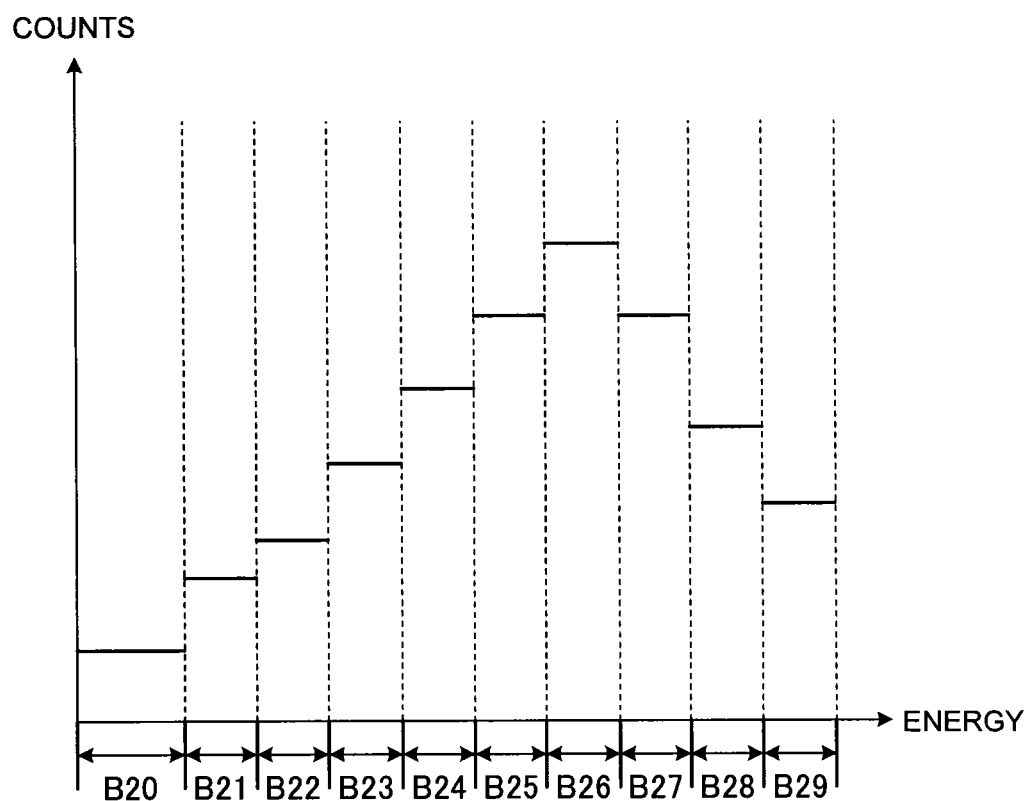
FIG. 3 is a chart of another example of a photon counting result.

These aspects will be explained, with reference to FIGS. 2 to 4. The vertical axes in FIGS. 2 to 4 express counting results of photons counted by the data acquiring unit 14. The horizontal axes in FIGS. 2 to 4 express examples of energy bands for which the photons are counted by the data acquiring unit 14. FIGS. 2 to 4 illustrate the counting results of the photons derived from the X-rays that are detected by one detecting element included in the X-ray detector 13.

In the example in FIG. 2, the data acquiring unit 14 equally divides a counting-target energy band into seven energy bands B10 to B16 and counts the photons for each of the energy bands. For example, the data acquiring unit 14 counts the photons having an energy level included in the energy band B10. Similarly, the data acquiring unit 14 counts the photons having an energy level included in each of the energy bands B11 to B16 as well.

A viewing target which the operator (the viewer) of the X-ray CT apparatus 1 desires to view may vary depending on the image taking mode being used. For example, when a contrast agent image taking process is set as the image taking mode, the operator may desire to view an X-ray CT image in which iodine contained in the contrast agent and other substances are rendered discriminately. The reason is that, generally speaking, the operator desires to view the site enhanced by the contrast agent. In other words, when the image taking mode is set to be a contrast agent image taking process, the substance of interest for the operator is iodine, while the other substances such as calcium are considered to be substances that are not of interest. However, iodine and calcium (bones and lime in blood vessels) and the like have similar X-ray transmissivity levels. Thus, in the example in FIG. 2, iodine and calcium may belong to mutually the same energy band (e.g., the energy band B13). In that situation, it is difficult for the X-ray CT apparatus 1 to reconstruct an X-ray CT image in which iodine and calcium are rendered discriminately, and it is therefore difficult to provide an X-ray CT image desired by the operator.

Further, not only when a contrast agent image taking process is selected as the setting, but also when a site specified image taking process using bones as an image taking target is selected as the setting, the operator may desire to view an X-ray CT image in which the bones and other substances are rendered discriminately. In that situation also, if the bones and the other substances belong to mutually the same energy band, it is difficult for the X-ray CT apparatus 1 to provide an X-ray CT image desired by the operator.

To cope with this situation, it is possible to configure the data acquiring unit 14 so as to divide the counting-target energy band into smaller sections and to count the photons for each of the sectioned energy bands, as illustrated in the example in FIG. 3. In the example in FIG. 3, the data acquiring unit 14 divides the counting-target energy band into ten energy bands B20 to B29. In the example in FIG. 3, even if substances such as iodine and calcium have similar transmissivity levels, the photons representing the substances are expected to belong to mutually-different energy bands among the plurality of energy bands resulting from the dividing into the sections. For example, it is expected that iodine belongs to the energy band B24, while another substance such as calcium belongs to the energy band B25. As a result, the X-ray CT apparatus 1 is able to provide an X-ray CT image desired by the operator (e.g., an X-ray CT image in which iodine and calcium are rendered discriminately).

In the example in FIG. 3, however, because the number of energy bands for which the photon counts are obtained increases, the amount of data transferred from the data acquiring unit 14 to the data storage unit 34 also increases. More specifically, in the example in FIG. 3, the amount of data transferred from the data acquiring unit 14 to the data storage unit 34 is 1.4 or more times larger than that in the example in FIG. 2. As mentioned above, because the data acquiring unit 14 and the data storage unit 34 are connected to each other by the contactless data transfer path, the increase in the data amount leads to a delay in the transfer from the data acquiring unit 14 to the data storage unit 34, pressure on the storage capacity of the data storage unit 34, an increase in the load in the reconstructing process, and the like. Thus, a delay will occur in the time period between when the subject P is scanned and when the X-ray CT image is reconstructed.

To address this situation, the X-ray CT apparatus 1 according to the first embodiment first counts the photons for each of the energy bands B20 to B29 resulting from the dividing into the sections, as illustrated in the example in the upper part of FIG. 4, and subsequently aggregates the photon counts of some of the energy bands, as illustrated in the example in the lower part of FIG. 4. In this situation, the X-ray CT apparatus 1 determines the energy bands of which the photon counts are aggregated, in accordance with the image taking mode input by the operator. More specifically, in accordance with the image taking mode set by the operator, the X-ray CT apparatus 1 uses a photon count obtained for a smaller energy band resulting from the dividing into the sections as the counting result with respect to the photons representing a substance desired to be discriminated from other substances. In contrast, the X-ray CT apparatus 1 uses a sum of photon counts obtained for some of the energy bands resulting from the dividing into the sections as the counting result with respect to the photons representing substances having less need to be discriminated from other substances.

For instance, in the example in FIG. 4, it is assumed that the operator has set the image taking mode to be a "contrast agent image taking process". Also, the energy level of the photons representing iodine or the like that is desired to be discriminated from other substances in the contrast agent image taking process is assumed to be substantially included in the energy bands B24 and B27 illustrated in the upper part of FIG. 4. In other words, when the image taking mode is a "contrast agent image taking process", it is assumed that the substances represented by the photons having the energy levels included in the energy bands B20 to B23, B25, B26, B28, and B29 have less need to be discriminated from other substances.

In that situation, the X-ray CT apparatus 1 according to the first embodiment, for example, calculates a sum of the photon counts for the energy bands B21 to B23 as the photon count for an energy band B31 corresponding to the energy bands B21 to B23. Similarly, the X-ray CT apparatus 1 calculates a sum of the photon counts for the energy bands B25 and B26 as the photon count for an energy band B33 (corresponding to the energy bands B25 and B26). Also, the X-ray CT apparatus 1 calculates a sum of the photon counts for the energy bands B28 and B29 as the photon count for an energy band B35 (corresponding to the energy bands B28 and B29). Further, the X-ray CT apparatus 1 uses the photon count obtained for the energy band B20 resulting from the dividing into the sections as the photon count for an energy band B30. Similarly, the X-ray CT apparatus 1 uses the photon count obtained for the energy band B24 as the photon count for an energy band B32 and uses the photon count obtained for the energy band B27 as the photon count for an energy band B34.

With this arrangement, the X-ray CT apparatus 1 according to the first embodiment is able to reconstruct an X-ray CT image in which iodine and other substances are rendered discriminately and is therefore able to provide the X-ray CT image desired by the operator. Further, as illustrated in the example in the lower part of FIG. 4, because the number of energy bands for which the photon counts are obtained is smaller than that in the example in FIG. 3, the X-ray CT apparatus 1 according to the first embodiment is able to reduce the amount of data transferred from the data acquiring unit 14 to the data storage unit 34. More specifically, the data size (the number of bits) transferred from the data acquiring unit 14 to the data storage unit 34 with respect to one energy band is fixed. In other words, the data for a single energy band is constant. Thus, the amount of data transferred from the data acquiring unit 14 to the data storage unit 34 is determined by the number of energy bands. Accordingly, because the X-ray CT apparatus 1 according to the first embodiment reduces the number of energy bands for which the data is transferred, the X-ray CT apparatus 1 is able to reduce the amount of data transferred from the data acquiring unit 14 to the data storage unit 34. In the example illustrated in the lower part of FIG. 4, the amount of data is 0.6 times smaller than (i.e., 60% of) that in the example in FIG. 3. Thus, the X-ray CT apparatus 1 according to the first embodiment is able to prevent the delay in the data transfer, the pressure on the storage capacity of the data storage unit 34, the increase in the load in the reconstructing process, and the like. The X-ray CT apparatus 1 is therefore able to shorten the time period between when the subject P is scanned and when the X-ray CT image is reconstructed.

In the example in FIG. 4, the X-ray CT apparatus 1 counts the photons for each of the energy bands resulting from the dividing into the ten sections and acquires the counting results corresponding to the six energy bands by aggregating the obtained photon counts. Alternatively, however, it is acceptable to configure the X-ray CT apparatus 1 to count the photons for each of the energy bands resulting from the dividing into more or less than ten sections. It is also acceptable to configure the X-ray CT apparatus 1 to acquire photon counting results corresponding to more or less than six energy bands, by aggregating the photon counts.

Figure 5:
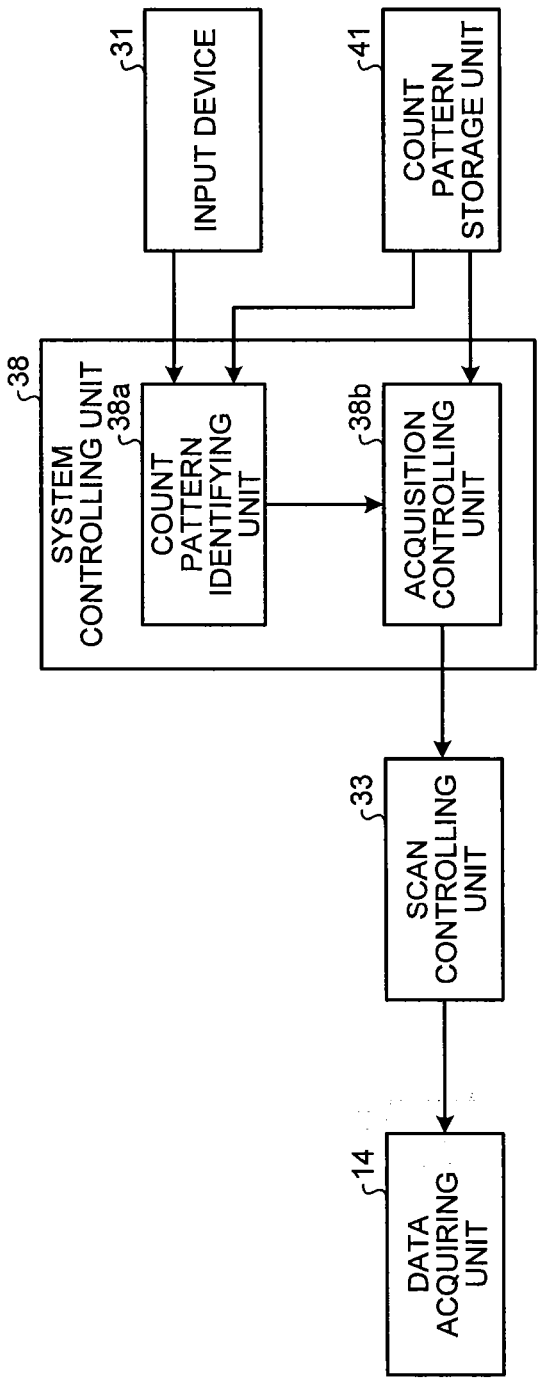
FIG. 5 is a block diagram of an exemplary configuration of a relevant part of the X-ray CT apparatus according to the first embodiment.

FIG. 5 is a block diagram of an exemplary configuration of a relevant part of the X-ray CT apparatus 1 according to the first embodiment. A count pattern storage unit 41 is configured with, for example, a semiconductor memory element such as a RAM or a flash memory, a hard disk, an optical disk, or the like. The count pattern storage unit 41 is configured to store therein the image taking modes that can be set by the operator and count patterns that are patterns of energy bands obtained by the dividing when the photons are counted, while keeping the image taking modes and the count patterns in correspondence with one another. In the example illustrated in the lower part of FIG. 4, the count pattern storage unit 41 stores therein, as a count pattern, the smallest energy value and the largest energy value (i.e., an energy range width) for each of the energy bands B30 to B35, in correspondence with the image taking mode of "contrast agent image taking process".

A count pattern identifying unit 38a included in the system controlling unit 38 is configured to identify a count pattern (sections of energy bands) to be used when the photons are counted by the data acquiring unit 14. More specifically, when an image taking mode has been set by the operator via the input device 31, the count pattern identifying unit 38a obtains the count pattern corresponding to the image taking mode out of the count pattern storage unit 41. For example, when a "contrast agent image taking process" is set as the image taking mode by the operator, the count pattern identifying unit 38a obtains the count pattern indicating the energy bands B30 to B35 illustrated in the lower part of FIG. 4, out of the count pattern storage unit 41.

In accordance with an image taking condition under which an image taking process is performed on the subject P, an acquisition controlling unit 38b included in the system controlling unit 38 controls the data acquiring unit 14, in such a manner that the energy bands including the energy levels of the photons representing substances that are not of interest are each wider than the energy band including the energy level of the photons representing a substance of interest. More specifically, the acquisition controlling unit 38b controls the data acquiring unit 14 so as to count the photons according to the count pattern identified by the count pattern identifying unit 38a. For example, let us assume that the count pattern identifying unit 38a has identified the energy bands B30 to B35 illustrated in the lower part of FIG. 4 as a count pattern. In that situation, the acquisition controlling unit 38b controls the data acquiring unit 14 via the scan controlling unit 33 so as to count the photons for each of the energy bands B30 to B35.

The data acquiring unit 14 first counts the photons for each of the energy bands resulting from dividing the counting-target energy band into the predetermined number of sections and subsequently aggregates the photon counts in units of energy bands specified by the acquisition controlling unit 38b. For example, after counting the photons for each of the energy bands resulting from the dividing into the ten sections as illustrated in the example in the upper part of FIG. 4, the data acquiring unit 14 acquires the photon counts for the six energy bands as the counting results, by aggregating the photon counts as illustrated in the example in the lower part of FIG. 4. It is assumed that the number of sections (e.g., ten sections) into which the energy band is divided is determined by the system in advance.

Figure 6:
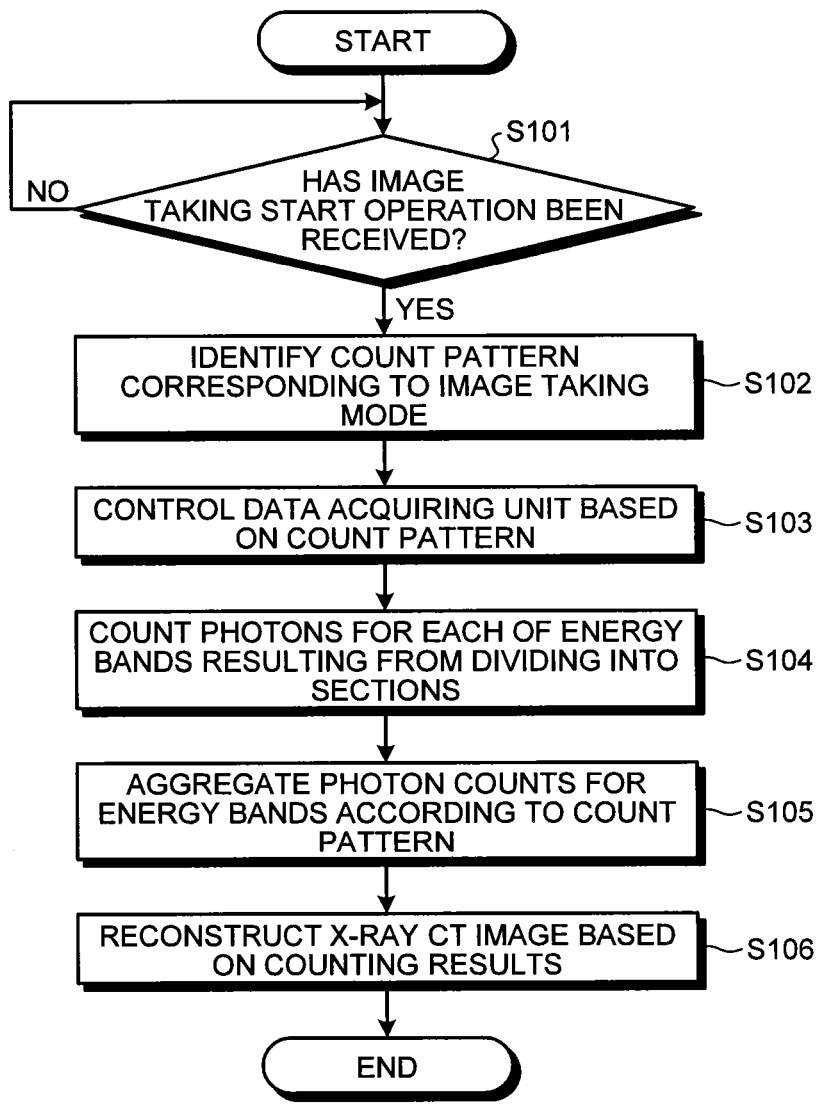
FIG. 6 is a flowchart of a processing procedure performed by the X-ray CT apparatus according to the first embodiment.

FIG. 6 is a flowchart of a processing procedure performed by the X-ray CT apparatus 1 according to the first embodiment. As illustrated in FIG. 6, the X-ray CT apparatus 1 determines whether an image taking start operation has been received via the input device 31 (step S101). In this situation, if no image taking start operation has been received (step S101: No), the X-ray CT apparatus 1 stands by until an image taking start operation is received.

On the contrary, if an image taking start operation has been received (step S101: Yes), the system controlling unit 38 performs processes described below. In that situation, the system controlling unit 38 receives a setting of the image taking mode from the operator.

More specifically, the count pattern identifying unit 38a included in the system controlling unit 38 identifies the count pattern corresponding to the image taking mode set by the operator, by referring to the count pattern storage unit 41 (step S102). Subsequently, the acquisition controlling unit 38b controls the data acquiring unit 14 so as to count the photons according to the count pattern identified by the count pattern identifying unit 38a (step S103).

The data acquiring unit 14 controlled by the acquisition controlling unit 38b counts the photons for each of the energy bands resulting from the dividing into the sections (step S104). The data acquiring unit 14 counts the photons for each of the energy bands resulting from the dividing into the sections, with respect to the detecting elements included in the X-ray detector 13. Further, according to the count pattern instructed by the acquisition controlling unit 38b, the data acquiring unit 14 aggregates the photon counts for the energy bands resulting from the dividing into the sections (step S105). After that, the data acquiring unit 14 transmits the photon counts corresponding to the aggregated groups to the data storage unit 34 as the counting results. Accordingly, an X-ray CT image is reconstructed by using the counting results stored in the data storage unit 34 (step S106).

As explained above, according to the first embodiment, it is possible to reduce the amount of data transmitted from the data acquiring unit 14 to the data storage unit 34 and to reconstruct the X-ray CT image desired by the operator.

In the first embodiment described above, the example is explained in which the photons are first counted by the data acquiring unit 14 for each of the energy bands (e.g., the energy bands B20 to B29) resulting from the dividing into the sections, and subsequently the counting results are aggregated. However, another arrangement is acceptable in which, instead of counting the photons for each of the energy bands resulting from the dividing into the sections, the data acquiring unit 14 counts the photons for each of the energy bands obtained after the control is exercised by the acquisition controlling unit 38b. For example, if the control is exercised so that the photons are counted for each of the energy bands B30 to B35 as illustrated in the lower part of FIG. 4, the data acquiring unit 14 may directly count the photons for each of the energy bands B30 to B35, instead of counting the photons for each of the energy bands B20 to B29 illustrated in the upper part of FIG. 4.

As a result, it is possible to reduce the load in the photon counting process performed by the data acquiring unit 14 (e.g., the ADCs). It is therefore possible to make the scanning process performed by the X-ray CT apparatus 1 faster. More specifically, when the data acquiring unit 14 counts the photons by employing the comparator or the like, the larger the number of energy bands resulting from the dividing into the sections is, the longer period of time it takes to perform the counting process, because the number of comparison targets to be compared with the energy levels of the photons increases. For example, if the energy band is divided into ten sections, the data acquiring unit 14 needs to compare ten values at maximum with the energy levels of the photons detected by the X-ray detector 13. In contrast, when counting the photons for each of the six energy bands B30 to B35 as described in the example above, the data acquiring unit 14 needs to compare six values at maximum with the energy levels of the photons. It is therefore possible to shorten the time period required by the counting process.

Further, the data acquiring unit 14 according to the first embodiment does not necessarily have to transmit, to the data storage unit 34, all of the photon counts obtained for the energy bands resulting from the dividing into the sections. More specifically, as illustrated in an example in the lower part of FIG. 7, it is acceptable to configure the data acquiring unit 14 to transmit a part of the photon counts obtained for the energy bands resulting from the dividing into the sections, to the data storage unit 34. In the example in FIG. 7, the data acquiring unit 14 counts the photons for the energy bands B20 to B29, uses the photon count obtained for the energy band B24 as the counting result for an energy band B32, uses the photon count obtained for the energy band B27 as the counting result for an energy band B34, and uses a sum of the photon counts obtained for the energy bands B25 and B26 as the counting result for an energy band B33 and thus transmits the photon counts for the energy bands B32 to B34 to the data storage unit 34. As a result, the X-ray CT apparatus 1 is able to reduce the amount of data transferred from the data acquiring unit 14 to the data storage unit 34.

In the example in FIG. 7, it is assumed that the data acquiring unit 14 is controlled by the acquisition controlling unit 38b so as to count the photons for the energy bands B32 to B34. Alternatively, in the example in FIG. 7, it is also acceptable to configure the data acquiring unit 14 so as to directly count the photons for the energy bands B32 to B34 similarly to the example described above, instead of counting the photons for the energy bands B20 to B29. With this arrangement, because the data acquiring unit 14 does not need to obtain such photon counts that do not need to be transmitted to the data storage unit 34, it is possible to further shorten the time period required by the counting process.

Second Embodiment

Figure 8:
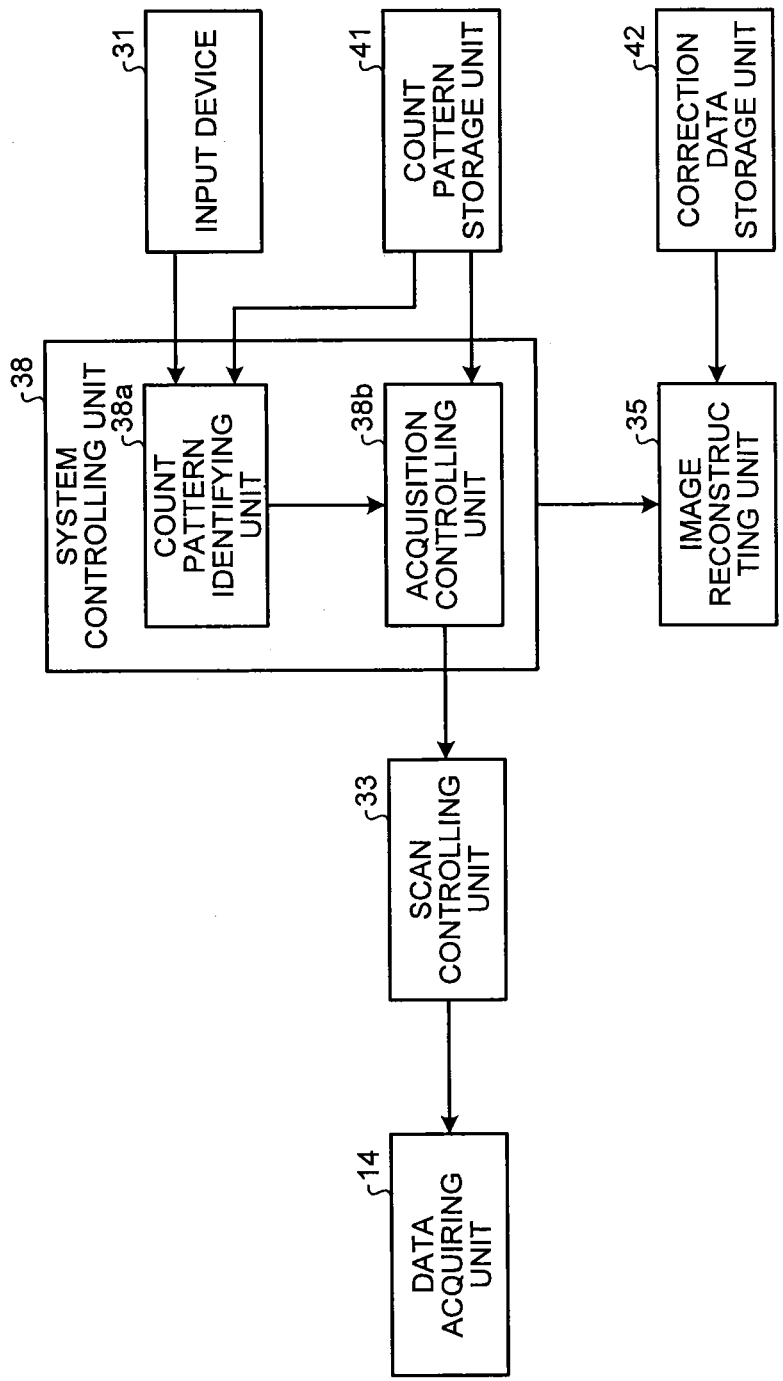
FIG. 8 is a block diagram of an exemplary configuration of a relevant part of an X-ray CT apparatus according to a second embodiment.

FIG. 8 is a block diagram of an exemplary configuration of a relevant part of the X-ray CT apparatus 1 according to a second embodiment. A correction data storage unit 42 is configured with, for example, a semiconductor memory element such as a RAM or a flash memory, a hard disk, an optical disk, or the like and is configured to store therein correction data that is used when an offset correction or the like is performed by the image reconstructing unit 35. More specifically, the correction data storage unit 42 is configured to store therein the correction data obtained as a result of the X-ray CT apparatus 1 taking an image of a phantom (water or the like). When the examined subject P is a phantom, because an ideal value of the count information to be acquired by the data acquiring unit 14 is known, it is possible to obtain the correction data used for correcting errors occurring due to individual differences in the X-ray detector 13, the data acquiring unit 14, and the like, by comparing the known ideal value with the count information actually acquired by the data acquiring unit 14.

In this situation, to obtain the correction data to be stored into the correction data storage unit 42, the data acquiring unit 14 counts the photons while the energy band is divided into sections, like in the example illustrated in the upper part of FIG. 4. More specifically, when the widths of the energy bands resulting from the dividing into the sections are determined by the system in advance, the data acquiring unit 14 performs a counting process for each of the energy bands resulting from the dividing into the sections and having the determined widths. As a result, by comparing the photon counts obtained for the energy bands by the data acquiring unit 14, with the known ideal photon counts for the energy bands, the X-ray CT apparatus 1 is able to obtain the correction data for the energy bands. The correction data storage unit 42 stores therein the correction data for the energy bands obtained in this manner. For example, the correction data storage unit 42 stores therein the correction data corresponding to the energy bands for each of the detecting elements included in the X-ray detector 13. In the example illustrated in the upper part of FIG. 4, the correction data storage unit 42 stores therein the correction data corresponding to the energy bands B20 to B29.

Further, the image reconstructing unit 35 performs various types of correcting processes such as an offset correction, by using the correction data stored in the correction data storage unit 42. Because the correction data storage unit 42 stores therein the correction data for each of the energy bands resulting from the dividing into the sections, the image reconstructing unit 35 is able to perform the correcting processes, no matter how the photon counts are aggregated by the data acquiring unit 14. For example, let us discuss an example in which the correction data storage unit 42 stores therein pieces of correction data R20 to R29 corresponding to the energy bands B20 to B29, respectively. In that situation, if the photon counts for the energy bands B21 to B23 are aggregated, the image reconstructing unit 35 uses the pieces of correction data R21 to R23 corresponding to the energy bands B21 to B23 in order to correct those photon counts. For example, the image reconstructing unit 35 corrects the aggregated photon counts by using an average value of the pieces of correction data R21 to R23, a sum of the results obtained by multiplying the pieces of correction data R21 to R23 with a weight coefficient, or the like.

As explained above, according to the second embodiment, it is possible to, similarly to the first embodiment, reduce the amount of data transmitted from the data acquiring unit 14 to the data storage unit 34 and to reconstruct an X-ray CT image desired by the operator. Further, it is possible to correct the photon counts aggregated by the data acquiring unit 14.

In the second embodiment described above, the example is explained in which the correction data storage unit 42 stores therein the correction data for each of the energy bands resulting from the dividing into the sections. However, it is also acceptable to configure the correction data storage unit 42 so as to store therein the correction data for the energy bands corresponding to each image taking mode, in correspondence with the image taking modes stored in the count pattern storage unit 41. For example, let us assume that the count pattern storage unit 41 stores therein, as a pattern of energy bands, the energy bands B30 to B35 illustrated in the lower part of FIG. 4, in correspondence with the image taking mode of "contrast agent image taking process". In that situation, it is acceptable to configure the correction data storage unit 42 so as to store therein the correction data corresponding to each of the energy bands B30 to B35, in correspondence with the image taking mode of "contrast agent image taking process". Further, it is acceptable to configure the image reconstructing unit 35 so as to obtain the correction data corresponding to the image taking mode set by the operator out of the correction data storage unit 42 and to correct the photon counting results obtained by the data acquiring unit 14 by using the obtained correction data.

In the first and the second embodiments described above, the example is explained in which the energy bands of which the photon counts are aggregated change in accordance with the image taking mode. It is, however, also expected that the energy bands of which the photon counts are aggregated change also when the voltage applied to the X-ray tube 12 is changed at a high speed, or the like. In that situation, it is also acceptable to configure the count pattern storage unit 41 so as to store therein the count patterns in correspondence with, for example, speeds at which the voltage applied to the X-ray tube 12 is changed. Further, it is acceptable to configure the count pattern identifying unit 38a so as to obtain a count pattern corresponding to the changing speed of the voltage applied to the X-ray tube 12 out of the count pattern storage unit 41 and to configure the acquisition controlling unit 38b so as to control the data acquiring unit 14 so as to perform the photon counting process according to the count pattern obtained by the count pattern identifying unit 38a.

Further, the constituent elements of the devices illustrated in the drawings are based on functional concepts. Thus, it is not necessary to physically configure the elements as indicated in the drawings. In other words, the specific mode of distribution and integration of the devices is not limited to those illustrated in the drawings. It is acceptable to functionally or physically distribute or integrate all or a part of the devices in any arbitrary units, depending on various loads and the status of use. Further, all or an arbitrary part of the processing functions performed by the devices may be realized by a CPU and a computer program that is analyzed and executed by the CPU or may be realized as hardware using wired logic.

Furthermore, it is possible to realize the X-ray CT image reconstructing method explained in any of the exemplary embodiments above by causing a computer such as a personal computer or a workstation to execute an image reconstructing computer program prepared in advance. It is possible to distribute such an image reconstructing computer program via a network such as the Internet. Further, the computer program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, and may be executed as being read by a computer from the recoding medium.

As explained above, according to aspects of the first and the second embodiments, it is possible to reduce the photon data count amount.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a detector configured to detect X-rays that have passed through a subject;
   a data acquiring unit configured to, for each of predetermined energy bands, count photons having an energy level included in the predetermined energy band, from among photons derived from the X-rays detected by the detector;
   an acquisition controlling unit configured to control the data acquiring unit in such a manner that energy bands including an energy level of photons corresponding to a substance that is not of interest have a width larger than a width of an energy band including an energy level of photons corresponding to a substance of interest, in accordance with an image taking condition under which an image taking process is performed on the subject; and
   an image reconstructing unit configured to reconstruct an X-ray CT image by using a counting result obtained by the data acquiring unit controlled by the acquisition controlling unit.

2. The X-ray CT apparatus according to claim 1, wherein, after dividing an entire counting-target energy band into first energy bands and counting photons for each of the first energy bands, the data acquiring unit calculates a sum of photon counting results for a plurality of the first energy bands that are included in a specified part of the entire counting-target energy band, as a photon counting result for a second energy band.

3. The X-ray CT apparatus according to claim 2, further comprising:
   a count pattern storage unit configured to store therein patterns of energy bands for which the photons are counted, in correspondence with image taking modes in which image taking processes are performed on the subject, wherein
   the acquisition controlling unit obtains a pattern of energy bands corresponding to an image taking condition under which the image taking process is performed on the subject, from the count pattern storage unit, and controls the data acquiring unit so as to count the photons based on the obtained pattern of energy bands.

4. The X-ray CT apparatus according to claim 3, further comprising:
a correction data storage unit configured to store therein, for each of first energy bands obtained by dividing an entire counting-target energy band into sections, correction data used for correcting a counting result acquired by the data acquiring unit for at least one of the first energy bands, wherein
the image reconstructing unit obtains, from the correction data storage unit, correction data corresponding to the first energy bands that are included in one of the energy bands for which the photons are counted by the data acquiring unit and corrects a photon counting result for the one energy band by using the correction data.

5. The X-ray CT apparatus according to claim 2, further comprising:
a correction data storage unit configured to store therein, for each of the first energy bands obtained by dividing an entire counting-target energy band into sections, correction data used for correcting a counting result acquired by the data acquiring unit for at least one of the first energy bands, wherein
the image reconstructing unit obtains, from the correction data storage unit, correction data corresponding to the first energy bands that are included in one of the energy bands for which the photons are counted by the data acquiring unit and corrects a photon counting result for the one energy band by using the correction data.

6. The X-ray CT apparatus according to claim 2, wherein the data acquiring unit is further configured to send counting results only for each second energy band and each of the first energy bands corresponding to a substance of interest to a data storage unit.

7. The X-ray CT apparatus according to claim 1, wherein the data acquiring unit counts the photons for each of energy bands specified by the acquisition controlling unit.

8. The X-ray CT apparatus according to claim 7, further comprising:
a count pattern storage unit configured to store therein patterns of energy bands for which the photons are counted, in correspondence with image taking modes in which image taking processes are performed on the subject, wherein
the acquisition controlling unit obtains a pattern of energy bands corresponding to an image taking condition under which the image taking process is performed on the subject, from the count pattern storage unit, and controls the data acquiring unit so as to count the photons based on the obtained pattern of energy bands.

9. The X-ray CT apparatus according to claim 8, further comprising:
a correction data storage unit configured to store therein, for each of first energy bands obtained by dividing an entire counting-target energy band into sections, correction data used for correcting a counting result acquired by the data acquiring unit for at least one of the first energy bands, wherein
the image reconstructing unit obtains, from the correction data storage unit, correction data corresponding to the first energy bands that are included in one of the energy bands for which the photons are counted by the data acquiring unit and corrects a photon counting result for the one energy band by using the correction data.

10. The X-ray CT apparatus according to claim 7, further comprising:
a correction data storage unit configured to store therein, for each of first energy bands obtained by dividing an entire counting-target energy band into sections, correction data used for correcting a counting result acquired by the data acquiring unit for at least one of the first energy bands, wherein
the image reconstructing unit obtains, from the correction data storage unit, correction data corresponding to the first energy bands that are included in one of the energy bands for which the photons are counted by the data acquiring unit and corrects a photon counting result for the one energy band by using the correction data.

11. The X-ray CT apparatus according to claim 1, further comprising:
a count pattern storage unit configured to store therein patterns of energy bands for which the photons are counted, in correspondence with image taking modes in which image taking processes are performed on the subject, wherein
the acquisition controlling unit obtains a pattern of energy bands corresponding to an image taking condition under which the image taking process is performed on the subject, from the count pattern storage unit, and controls the data acquiring unit so as to count the photons based on the obtained pattern of energy bands.

12. The X-ray CT apparatus according to claim 11, further comprising:
a correction data storage unit configured to store therein, for each of first energy bands obtained by dividing an entire counting-target energy band into sections, correction data used for correcting a counting result acquired by the data acquiring unit for at least one of the first energy bands, wherein
the image reconstructing unit obtains, from the correction data storage unit, correction data corresponding to the first energy bands that are included in one of the energy bands for which the photons are counted by the data acquiring unit and corrects a photon counting result for the one energy band by using the correction data.

13. The X-ray CT apparatus according to claim 11, wherein an energy range of the obtained pattern is smaller than an entire counting-target energy band.

14. The X-ray CT apparatus according to claim 1, further comprising:
a correction data storage unit configured to store therein, for each of first energy bands obtained by dividing an entire counting-target energy band into sections, correction data used for correcting a counting result acquired by the data acquiring unit for at least one of the first energy bands, wherein
the image reconstructing unit obtains, from the correction data storage unit, correction data corresponding to the first energy bands that are included in one of the energy bands for which the photons are counted by the data acquiring unit and corrects a photon counting result for the one energy band by using the correction data.

15. An X-ray CT apparatus comprising:
an X-ray source configured to expose a subject with X-rays;
a data acquiring unit configured to, for each of first energy bands, count photons having an energy level included in each of the first energy bands, from photons derived from the X-rays;
an acquisition controlling unit configured to control the data acquiring unit such that photon counts of first energy bands including energy levels of photons corresponding to a substance that is not of interest are aggregated into an aggregated photon count;

a storage unit storing count data from the data acquiring unit; and an image reconstructing unit configured to reconstruct an X-ray CT image by using a counting result obtained by the data acquiring unit controlled by the acquisition controlling unit, wherein the data acquiring unit sends, as the count data, only photon counts of first bands including energy levels of photons corresponding to a substance of interest to the storage unit and the aggregated photon count.

16. The X-ray CT apparatus according to claim 15, further comprising:

a count pattern storage unit configured to store therein patterns of energy bands for which the photons are counted, in correspondence with image taking processes, wherein the acquisition controlling unit obtains a pattern of energy bands corresponding to the image taking process performed on the subject from the count pattern storage unit, and controls the data acquiring unit so as to count the photons based on the obtained pattern of energy bands.

17. The X-ray CT apparatus according to claim 16, wherein an energy range of the obtained pattern is smaller than an entire counting-target energy band.

18. An X-ray CT apparatus comprising:

an X-ray source configured to expose a subject with X-rays;

a count pattern storage unit configured to store therein patterns of energy bands for which photons are counted, in correspondence with image taking processes, the energy bands including a first band having an energy level of photons corresponding to a substance of interest and second energy bands each having energy levels of photons corresponding to a substance that is not of interest;

a data acquiring unit configured to count photons having an energy level included in the first and second energy bands;

an acquisition controlling unit configured to obtain one of the patterns corresponding to an image taking process performed on the subject from the count pattern storage unit, and control the data acquiring unit so as to count the photons of each first energy band and aggregate the counts of the second energy bands;

a storage unit storing count data from the data acquiring unit; and an image reconstructing unit configured to reconstruct an X-ray image by using a counting result obtained by the data acquiring unit, wherein the data acquiring unit sends, as the count data, only photon counts of first bands including energy levels of photons corresponding to a substance of interest to the storage unit and the aggregated photon count.

* * * * *